(12) United States Patent
Spinale et al.

(10) Patent No.: US 6,211,217 B1
(45) Date of Patent: *Apr. 3, 2001

(54) METHOD FOR REDUCING PERICARDIAL FIBROSIS AND ADHESION FORMATION

(75) Inventors: Francis G. Spinale, Charleston, SC (US); Marc de Gasparo, Rossemaison (CH)

(73) Assignee: Novartis AG, Basel (CH)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/270,412

(22) Filed: Mar. 16, 1999

(51) Int. Cl.$^7$ .................................................. A61K 31/41
(52) U.S. Cl. ............................................................ 514/381
(58) Field of Search ............................................. 514/381

(56) References Cited

U.S. PATENT DOCUMENTS

| | | | |
|---|---|---|---|
| 5,196,537 | 3/1993 | Reitz | 546/276 |
| 5,328,911 | 7/1994 | Miyake et al. | 514/303 |
| 5,451,591 | 9/1995 | Reitz | 514/337 |
| 5,451,593 | 9/1995 | Reitz | 514/340 |
| 5,498,722 | 3/1996 | Ross et al. | 548/315 |
| 5,506,238 | 4/1996 | Miyake et al. | 514/303 |
| 5,529,992 | 6/1996 | Weber | 514/175 |
| 5,591,762 | 1/1997 | Hauel et al. | 514/381 |
| 5,594,003 | 1/1997 | Hauel et al. | 514/300 |
| 5,602,127 | 2/1997 | Hauel et al. | 514/222 |
| 5,610,153 | 3/1997 | Bühlmeyer et al. | 514/211 |
| 5,614,519 | 3/1997 | Hauel et al. | 514/235 |
| 5,645,839 | 7/1997 | Chobanian et al. | 424/400 |
| 5,683,997 | 11/1997 | Bühlmeyer et al. | 514/213 |
| 5,684,007 | 11/1997 | Borer et al. | 514/255 |
| 5,703,110 | 12/1997 | Naka et al. | 514/396 |
| 5,705,517 | 1/1998 | Naka et al. | 514/381 |

FOREIGN PATENT DOCUMENTS

| | | |
|---|---|---|
| 2050723 | 3/1992 | (CA) . |
| 2057913 | 7/1997 | (CA) . |
| 93/20816 | 10/1993 | (WO) . |
| 95/33454 | 12/1995 | (WO) . |
| 96/40255 | 12/1996 | (WO) . |
| 96/40256 | 12/1996 | (WO) . |
| 96/40257 | 12/1996 | (WO) . |
| 96/40258 | 12/1996 | (WO) . |

OTHER PUBLICATIONS

Luft et al., Hypertension 33/1 II (212–218) (abstract), Jan. 1999.*

Folke et al. Hypertension, 33/1 Part 2, pp. 389–395 (abstract), Jan. 1999.*

Allen et al., The Society of Thoracic Surgeons, vol. 64, pp. 616–622 (1997).

Brink et al., J Mol Cell Cardiol, vol. 28, pp. 1789–1799 (1996).

Bunkenburg et al., Hypertension, vol. 18, No. 3, pp. 278–288 (1991).

Christenson et al., European Journal of Cardio–thoracic Surgery, vol. 11, pp. 129–133 (1997).

Criscione et al., Br. J. Pharmacol., vol. 110, pp. 761–771 (1993).

Chung et al., Kidney International, vol. 54, Suppl. 67, pp. S–95–S–99 (1998).

de Gesparo et al., Pharmacology & Toxicology, vol. 82, pp. 257–271 (1998).

Duvernoy et al., Thorac, cardiovasc. Surgeon, vol. 43, pp. 271–274 (1995).

Goldberg et al., Hypertension, vol. 25, No. 1, pp. 37–47 (1995).

Hurle et al., Ann Thorac Surg., vol. 63, pp. 1091–1094 (1997).

Moulder et al., J. Radiat. Biol., vol. 73, No. 4, pp. 415–421 (1998).

Nishimura et al., Kidney International, vol. 53, pp. 937–944 (1998).

Nkere et al., Thorac, cardiovasc. Surgeon, vol. 43, pp. 338–346 (1995).

Noyez et al., European Journal of Cardio–thoracis Surgery, vol. 11, pp. 528–532 (1997).

Ohkubo et al., Circulation, vol. 96, No. 11, pp. 3954–3962 (1997).

(List continued on next page.)

Primary Examiner—Phyllis G. Spivack
(74) Attorney, Agent, or Firm—Gregory D. Ferraro

(57) ABSTRACT

Disclosed are methods of reducing fibrosis and adhesion formation in a surgical patient wherein the $AT_1$ receptor antagonist, the compound (S)-N-(1-carboxy-2-methylprop-1-yl)-N-pentanoyl-N-[2'(1H-tetrazol-5-yl)biphenyl-4-yl-methyl]amine (valsartan) of formula

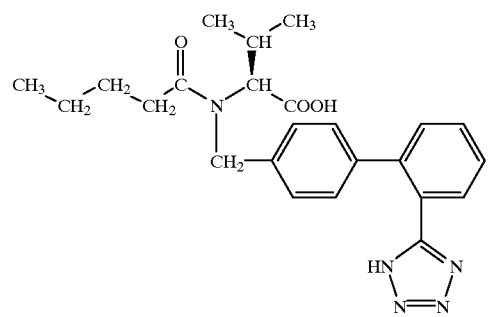

or a salt thereof, in particular a pharmaceutically acceptable salt thereof, is administered to the patient. In particular, disclosed are methods of reducing pericardial fibrosis and pericardial adhesion formation which results from cardiac surgery.

10 Claims, 3 Drawing Sheets

OTHER PUBLICATIONS

Ou et al., J Mol Cell Cardiol, vol. 28, pp. 1319–1327 (1996).
Reves et al., Circulation, vol. 66, No. 1, pp. 49–55, (1982).
Seeger et al., Journal of Surgical Research, vol. 68, pp. 63–66 (1997).
Spinale et al., Am. J. Physiol. vol. 261: (Heart Circ. Physiol, 30) H308–H318 (1991).
Spinale et al., Circulation Research, vol. 82, pp. 482–495 (1998).
Spinale et al., Circulation, vol. 96, No. 7, pp. 2385–2396 (1997).
Sun et al., Cardiovascular Research, vol. 31, pp. 518–525 (1996).
Sun et al., J Mol Cell Cardiol, vol. 29, pp 2001–2012 (1997).
Kurki et al., Ann Thorac Surg., vol. 61, pp 1740–1745 (1996).
Weber et al., Circulation, vol. 83, No. 6, pp. 1849–1865 (1991).
Weber et al., Int. J. Biochem. Cell Biol. vol. 29, pp. 31–42 (1996).
Weber et al., J. Am. Coll. Cardiol, vol. 20, No. 1, pp. 3–16 (1992).
Whittaker et al., Basic Res. Cardiol, vol. 89, pp. 397–410 (1994).
Tsutsumi et al., Circulation Research, vol. 83, No. 10, pp. 1035–1046 (1998).
Holtz, Gary, Modern Trends, vol. 41, No. 4, (1984).
Yaacobi et al., Journal of Surgical Research, vol. 55, pp. 422–426 (1993).
Janik et al., Arch Surg. vol. 117, pp. 1321–1324 (1982).
Reikerds et al., Eur. Surg. Res., vol. 19, pp. 62–64 (1987).
Salm et al., Arch Surg., vol. 121, pp. 462–467 (1986).
Salomon et al., J. Thorac Cardiovasc. Surg. vol. 100, pp. 250–260 (1990).
Wiseman et al., Journal of Surgical Research, vol. 53, pp. 362–368 (1992).
Ma et al., Kidney International, vol. 53, pp. 937–944 (1998).

\* cited by examiner

METHOD FOR REDUCING PERICARDIAL FIBROSIS AND ADHESION FORMATION

BACKGROUND

Fibrosis, the formation of excessive amounts of fibrotic or scar tissue, is a central issue in medicine. Scar tissue blocks arteries, immobilizes joints and damages internal organs, wreaking havoc on the body's ability to maintain vital functions. Every year, about 1.3 million people are hospitalized due to the damaging effects of fibrosis, yet doctors have few therapeutics to help them control this dangerous condition. Fibrosis can follow surgery in the form of adhesions, keloid tumors or hypertrophic (very severe) scarring. Fibrosis causes contractures and joint dislocation following severe burns, wounds or orthopedic injuries; it can occur in any organ and accompanies many disease states, such as hepatitis (liver cirrhosis), hypertension (heart failure), tuberculosis (pulmonary fibrosis), scleroderma (fibrotic skin and internal organs), diabetes (nephropathy) and atherosclerosis (fibrotic blood vessels). Ironically, the very process designed to repair the body can lead to dangerous complications. Like epoxy, scar tissue serves only a structural role. It fills in the gaps, but cannot contribute to the function of the organ in which it appears. For example, as fibrotic scar tissue replaces heart muscle damaged by hypertension, the heart becomes less elastic and thus less able to do its job. Similarly, pulmonary fibrosis causes the lungs to stiffen and decrease in size, a condition that can become life-threatening. Fibrotic growth can also proliferate and invade the healthy tissue that surrounds it even after the original injury heals. Too much scar tissue thus causes physiological roadblocks that disfigure, cripple or kill.

In most cases, fibrosis is a reactive process, and several different factors can apparently modulate the pathways leading to tissue fibrosis. Such factors include the early inflammatory responses, local increase in fibroblast cell populations, modulation of the synthetic function of fibroblasts, and altered regulation of the biosynthesis and degradation of collagen.

One of the most important pathologies for which fibrosis is a problematic factor is cardiac surgery. The number of patients undergoing cardiac surgery has been steadily increasing, and as a consequence, the number of cardiac reoperations has also increased.[1-6] It has been estimated that one out of every five patients undergoing coronary artery bypass surgery will require a reoperation.[3,4] Reoperative cardiac surgical procedures are associated with a significantly greater complication rate than that of the initial procedure.[5,6] For example, the post-operative complication rate following a reoperative coronary artery bypass procedure nearly doubles.[6] As a consequence, cardiac reoperations are associated with increased morbidity and mortality.[2-6] An important contributory factor for the increased complications with cardiac reoperations is the adhesions which form secondarily from the initial entry into the pericardium.[1-6] These fibrous adhesions begin to form immediately following the surgical procedure and consist of collagen and other extra cellular proteins.[7-9] It has been demonstrated in a number of cell systems that enhanced collagen synthesis can occur due to increased production of angiotensin II (Ang II) and subsequent activation of the Ang $AT_1$ receptors.[10,11] Moreover, increased production of Ang II has been directly demonstrated in fibrotic pericardium.[12] The post-operative period following cardiac surgery is associated with heightened neurohormonal stimulation, which in turn could potentially contribute to pericardial adhesion formation.[13]

The increased production of Ang II is due to the activation of the body's reninangiotensin-aldosterone system (RAAS). The enzyme cascade of the renin-angiotensin system (RAS) comprises a series of biochemical sequences. Angiotensinogen, a α2-macroglycoprotein, is split by the renin enzyme into the deca-peptide angiotensin I, which itself is biologically only very weakly active. The next step in the cascade is the removal of a further two amino acids by the action of the angiotensin-converting enzyme (ACE), bonded mainly in the endothelium, with formation of angiotensin II.

Angiotensin II interacts with specific receptors on the surface of the target cell. It has been possible to identify receptor subtypes which are termed e.g. $AT_1$- and $AT_2$-receptors. Great efforts have been made lately to identify substances that bind to $AT_1$-receptors. Such active ingredient (s)s are often termed angiotensin II antagonists. Because of the inhibition of the $AT_1$-receptor such antagonists can be used e.g. as antihypertensives or for the treatment of congestive heart failure.

The work of Brilla and Weber[21] report experiments in vitro, which clearly show the involvement of the $AT_1$ and $AT_2$ Ang receptors in the pathological effect of Ang II especially on fibroblasts because of collagen deposition and fibrotic lesions. These reports concluded that $AT_1$ receptor blockade may be valuable in preventing myocardial fibrosis or renal disease progression.

Many procedures have been attempted to treat fibrosis such as is disclosed in U.S. Pat. No. 5,645,839 issued to Chobanian on Jul. 8, 1997. The focus of this patent is the combined use of angiotensin inhibitors and nitric oxide stimulators for the treatment of myocardial fibrosis. This patent is directed to the concept that inhibition of angiotensin II production and enhanced nitric oxide production will reduce cardiovascular fibrosis. Cardiovascular fibrosis is defined as abnormal deposition of scar tissue due to naturally occurring disease processes such as myocardial fibrosis secondary to hypertension, arterial fibrosis due to arteriosclerosis, pulmonary fibrosis and scleroderma. Further, U.S. Pat. No. 5,529,992 issued to Weber on Jun. 25, 1996 discloses a method of using an aldosterone antagonist such as spironolactone, at a dosage which does not disrupt a patient's normal electrolyte and water-retention balance, to inhibit myocardial fibrosis, including left ventricular hypertrophy (LVH). U.S. Pat. No. 5,684,007 discloses a method for inhibiting cardiac fibroblast growth using a carbostyril derivative. This method is only demonstrated on cardiac cells in vitro. However, none of the known treatments are concerned with preventing fibrosis and the formation of adherences following surgery.

Due to the extreme debilitating effects of fibrosis, there is a need for a method to reduce surgical fibrosis and adhesion formation.

There is also a need for of a method for reducing pericardial fibrosis and adhesion formation following cardiac surgery.

Further, there is a need of a method for reducing fibrosis which results from induced pathological conditions in a patient.

There is also a need for a pharmaceutical composition comprising $AT_1$ receptor antagonists or a pharmaceutically acceptable salt thereof for reducing surgical fibrosis and adhesion formation.

SUMMARY

Toward these ends, and others, an aspect of the invention provides a method of reducing pericardial fibrosis and adhesion formation in a cardiac surgery patient comprising administering a therapeutically effective amount of an $AT_1$ receptor antagonist or a pharmaceutically acceptable salt thereof either alone or in combination with a pharmaceutically acceptable excipient wherein administration is prior to fibrosis and adherence formation.

In accordance with another aspect of the present invention provides a method of reducing fibrosis and adhesion formation in a patient following surgery comprising administering a therapeutically effective amount of an $AT_1$ receptor antagonist or a pharmaceutically acceptable salt thereof either alone or in combination with a pharmaceutically acceptable excipient wherein administration is prior to fibrosis and adherence formation.

More particularly the fibrosis which results from surgery includes surgery on the viscera, for example, stomach, small and large intestine, liver, biliary duct, pancreas, kidney, mesentery and peritoneum, surgery on the pelvic organs including surgery for a twisted ovarian cyst, ruptured tuboovarian abscess, ureteral stricture and an ectopic gestation.

In accordance with yet another embodiment of the present invention there is provided a method of reducing fibrosis and adhesion formation which results from induced pathological conditions which include, but are not limited to, drug-induced retroperitoneal fibrosis e.g. methysergide, post irradiation fibrosis, peritonitis and post-toxic peritonitis adhesiolysis comprising administering prior to the induced pathological condition a therapeutically effective amount of an $AT_1$ receptor antagonist or a pharmaceutically acceptable salt thereof either alone or in combination with a pharmaceutically acceptable excipient.

In accordance with still another aspect of the present invention, there is provided a method of reducing fibrosis and adhesion formation in a patient following surgery comprising administering a therapeutically effective amount of an $AT_1$ receptor antagonist or a pharmaceutically acceptable salt thereof either alone or in combination with a pharmaceutically acceptable excipient and stimulating the $AT_2$ receptor wherein administration and stimulation are prior to fibrosis and adherence formation.

Another aspect of the invention provides a pharmaceutical composition comprising an $AT_1$ receptor antagonist as an active ingredient(s) or a salt thereof wherein the pharmaceutical composition is administered for reducing surgical fibrosis and adhesion formation.

The $AT_1$ receptor antagonist may be administered alone or in combination with a pharmaceutically acceptable excipient to a patient by means including pulmonary absorption, injection, topical administration, oral administration, macromolecular targeting or release from an implant.

Other objects, features, advantages and aspects of the present invention will become apparent to those of skill from the following description. It should be understood, however, that the following description and the specific examples, while indicating preferred embodiments of the invention, are given by way of illustration only. Various changes and modifications within the spirit and scope of the disclosed invention will become readily apparent to those skilled in the art from reading the following description and from reading the other parts of the present disclosure.

BRIEF DESCRIPTION OF THE DRAWINGS

The following drawings depict certain embodiments of the invention. They are illustrative only and do not limit the invention otherwise disclosed herein.

DESCRIPTION

Figure 1A:
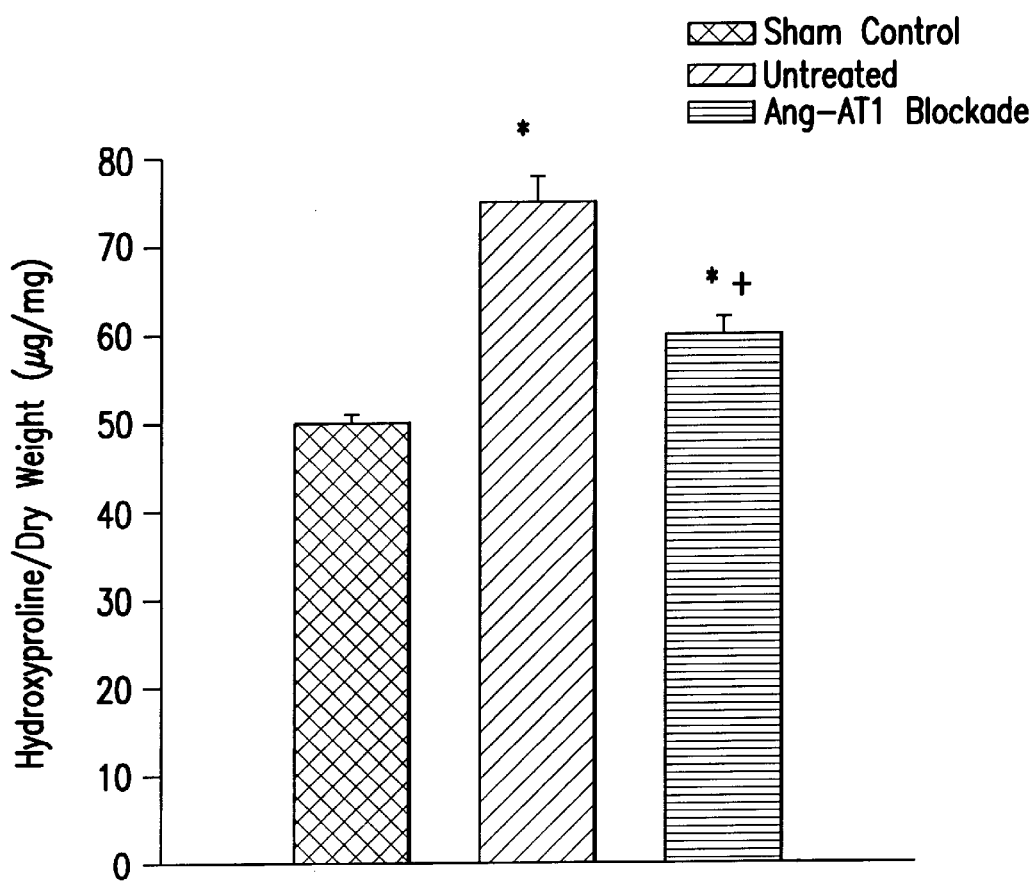
FIG. 1. Hydroxyproline, an amino acid found primarily in collagen, was determined in pericardial samples taken from sham control (n=6), 28 days following pericardiotomy with no treatment (untreated; n=5), and 28 days following pericardiotomy in which Ang $AT_1$ receptor blockade (Ang $AT_1$ blockade; n=5) was instituted during the entire post-operative period. TOP: Hydroxyproline content, determined $\mu$g/mg of dry pericardium, was increased 28 days following pericardiotomy, and was reduced with Ang $AT_1$ receptor blockade. BOTTOM: Hydroxyproline, as expressed as a percent of total pericardial protein, was increased, 28 days following pericardiotomy and normalized with Ang $AT_1$ receptor blockade. (*$p<0.05$ vs. sham control, +$p<0.05$ vs Ang $AT_1$ blockade)

In accordance with a preferred aspect of the invention there is provided a method of reducing pericardial fibrosis and adhesion formation resulting from cardiac surgery comprising administering a therapeutically effective amount of an $AT_1$ receptor antagonist or a pharmaceutically acceptable salt thereof either alone or in combination with a pharmaceutically acceptable excipient wherein administration is prior to fibrosis and adherence formation.

The term "$AT_1$ receptor antagonists" means an agent that interferes with the function, synthesis or catabolism of angiotensin II and includes, but is not limited to, compounds having the following structural features. The compounds which are listed in the European Pat. Application having the publication No. 443983 (EP 443983), in particular in the compound claims and the final products of the working examples, the subject-matter of which is hereby incorporated into the present application by reference to this publication.

Preference is given to (S)-N-(1-carboxy-2-methylprop-1-yl)-N-pentanoyl-N-[2'(1H-tetrazol-5-yl)biphenyl-4-ylmethyl]amine [Valsartan] of the formula

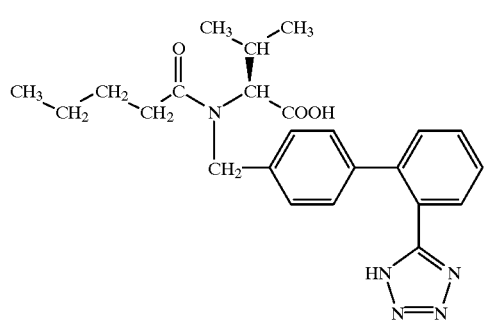

(I)

and its pharmaceutically utilizable salts.

The compounds which are listed in European Pat. Application having the publication No. 253310 (EP 253310), in particular in the compound claims and the final products of the working examples, are hereby incorporated into the present application by reference to this publication.

Preference is given to the compound [Losartan] of the following formula

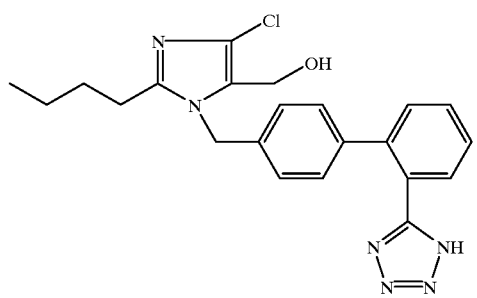

and its pharmaceutically utilizable salts.

The compounds listed in the European Pat. Application having the publication No. 403159 (EP 403159), in particular in the compound claims and the final products of the working examples, are hereby incorporated into the present application by reference to this publication.

Preference is given to the compound [Eprosartan] of the following formula

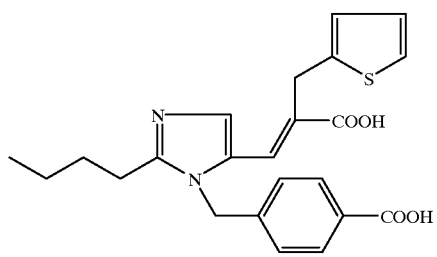

and its pharmaceutically utilizable salts.

The compounds listed in the PCT Pat. Application having the publication No. WO 91/14679, in particular in the compound claims and the final products of the working examples, are hereby incorporated into the present application by reference to this publication.

Preference is given to the compound [Irbesartan] of the following formula

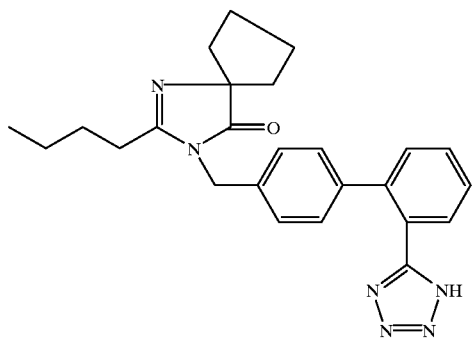

and its pharmaceutically utilizable salts.

The compounds listed in the European Pat. Application having the publication No. EP 420237 (EP 420237), in particular in the compound claims and the final products of the working examples, are hereby incorporated into the present application by reference to this publication.

Preference is given to the compound [E-1477] of the following formula

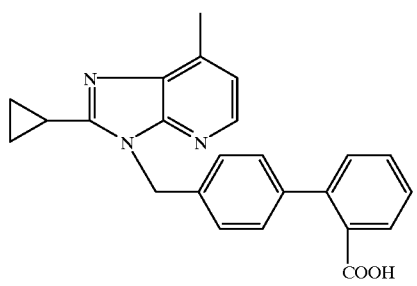

and its pharmaceutically utilizable salts.

The compounds listed in the European Pat. Application having the publication No. 502314 (EP 502314), in particular in the compound claims and the final products of the working examples, are hereby incorporated into the present application by reference to this publication.

Preference is given to the compound [Telmisartan] of the following formula

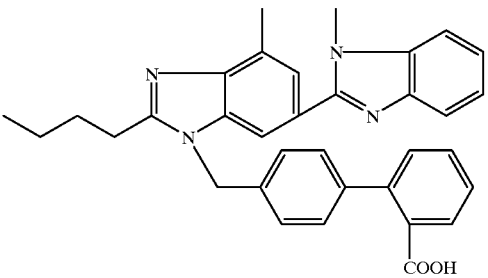

and its pharmaceutically utilizable salts.

The compounds listed in the European Pat. Application having the publication No. 459136 (EP 459136), in particular in the compound claims and the final products of the working examples, are hereby incorporated into the present application by reference to this publication.

Preference is given to the compound [Candesartan] of the following formula

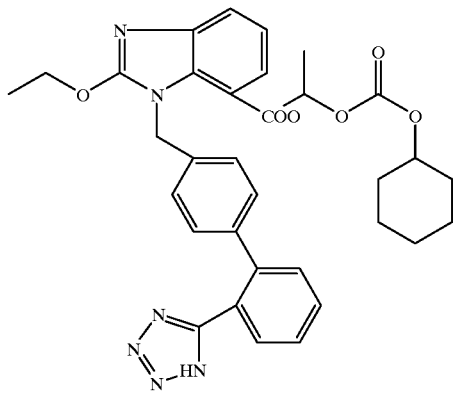

and its pharmaceutically utilizable salts.

The compounds listed in European Pat. Application having the publication No. 504888 (EP 504888), in particular in the compound claims and the final products of the working examples, are hereby incorporated into the present application by reference to this publication.

Preference is given to the compound [SC-52458] of the following formula

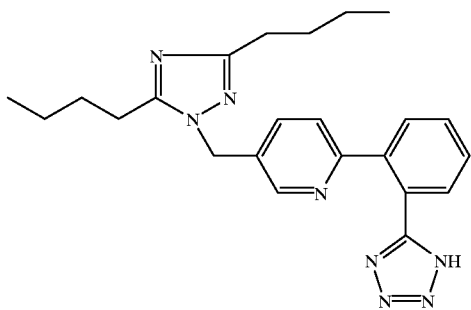

and its pharmaceutically utilizable salts.

The compounds listed in the European Pat. Application having the publication No. 514198 (EP 514198), in particular in the compound claims and the final products of the working examples, are hereby incorporated into the present application by reference to this publication.

Preference is given to the compound [Saprisartan] of the following formula

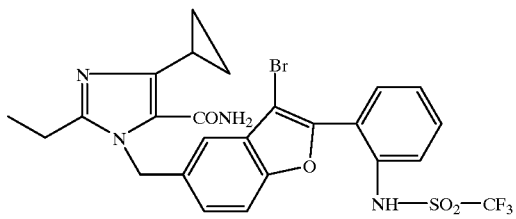

and its pharmaceutically utilizable salts.

The compounds listed in the European Pat. Application having the publication No. 475206 (EP 475206), in particular in the compound claims and the final products of the working examples, are hereby incorporated into the present application by reference to this publication.

Preference is given to the compound of the following formula

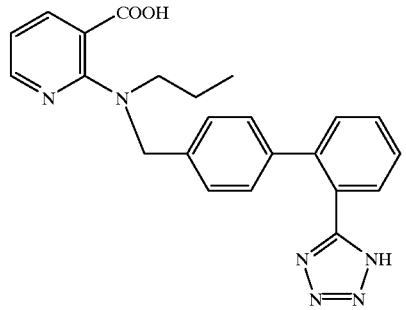

and its pharmaceutically utilizable salts.

The compounds listed in the PCT Pat. Application having the publication No. WO 93/20816, in particular in the compound claims and the final products of the working examples, are hereby incorporated into the present application by reference to this publication.

Preference is given to the compound [ZD-8731] of the following formula

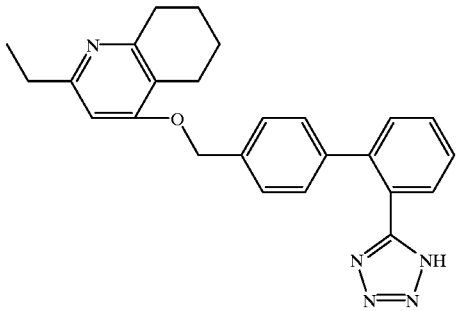

and its pharmaceutically utilizable salts.

Furthermore, the compounds listed in WO 94/13642, in particular in the compound claims and the final products of the working examples, are hereby incorporated into the present application by reference to this publication.

$AT_1$ receptor antagonists which, for example, possess at least one basic center can form acid addition salts. These are formed, for example, using strong inorganic acids, such as mineral acids, e.g. sulfuric acid, a phosphoric acid or a hydrohalic acid, using strong organic carboxylic acids, such as $C_1$–$C_4$alkanecarboxylic acids which are unsubstituted or substituted, for example, by halogen, e.g. acetic acid, such as saturated or unsaturated dicarboxylic acids, e.g. oxalic, malonic, succinic, maleic, fumaric, phthalic or terephthalic acid, such as hydroxycarboxylic acids, e.g. ascorbic, glycolic, lactic, malic, tartaric or citric acid, such as amino acids, e.g. aspartic or glutamic acid, or such as benzoic acid, or using organic sulfonic acids, such as $C_1$–$C_4$alkanesulfonic acids or arylsulfonic acids which are unsubstituted or substituted, for example, by halogen, e.g. methanesulfonic acid or p-toluenesulfonic acid. Examples of suitable salts with bases are metal salts, such as alkali metal or alkaline earth metal salts, e.g. sodium, potassium or magnesium salts, or salts with ammonia or an organic amine, such as morpholine, thiomorpholine, piperidine, pyrrolidine, a mono-, di- or tri-lower alkyl amine, e.g. ethyl-, tert-butyl-, diethyl-, diisopropyl-, triethyl-, tributyl- or dimethylpropyl-amines, or a mono-, di- or tri-hydroxy lower alkyl amine, e.g. mono-, di- or tri-ethanolamine. Furthermore, corresponding internal salts can be formed.

Valsartan is the preferred compound for use in the methods of the present invention. Moreover, the preferred time of administration of the compounds of the present invention for reducing fibrosis and adhesion formation is during surgery and is continued through the post-operative recovery period.

As used herein, the term "fibrosis" means those disorders that are caused by abnormal deposition of scar tissue. Fibrosis includes, but is not limited to, the formation of pericardial adhesions and deposition of collagen following the opening of the pericardium to access the heart. Fibrosis also includes deposition of scar tissue and adhesions following abdominal, pelvic, pleural and lung surgery and which result from induced pathological conditions.

Pericardial adhesions encountered at reoperation prevent easy access to the myocardium and result in difficult and blind dissections which can cause an increase in the duration of the procedure. [1,7,9] In the post-operative period, adhesion formation can adversely effect ventricular filling as well as the patency of the newly placed vascular conduits.[7] The majority of past studies which have attempted to reduce the clinical impact of pericardial adhesion formation have been focused upon the direct application of biodegradable lubricants or patches on the pericardial surface.[8,9] The results from an animal model of pericardial fibrosis suggests that Ang $AT_1$ receptor activation contributes to the development of pericardial thickening and collagen accumulation in the postoperative period. Thus, Ang $AT_1$ receptor inhibition provides a therapeutic strategy to reduce pericardial fibrosis and adhesion formation which is an important sequelae following cardiac surgical procedures, in particular the opening of the pericardium to access the heart.

The incidence of post-operative complications, morbidity and mortality greatly increase with cardiac surgical reoperations.[6] The basis for the increased risk with cardiac reoperations is likely multifactorial and includes increased patient age, co-morbidities, and the presence of left ventricular dysfunction. These pre-existing operative risk factors coupled with the extended operative time associated with cardiac reoperations are likely factors for the increased number of post-operative complications. Pericardial adhesions encountered at cardiac reoperation extend the surgical procedure time, and therefore have been identified as an important surgical risk factor. [2-5] In light of the fact that the need for cardiac reoperation, particularly that for coronary revascularization is increasing, interrupting pericardial fibrosis and adhesion formation following the initial cardiac surgical procedure is an important post-operative treatment strategy. The reduction of pericardial fibrosis following the initial surgical procedure may have particular clinical relevance to younger patients in which a future reoperation has a higher probability. In one aspect of the present invention orally bioavailable Ang $AT_1$ receptor antagonist, valsartan,[1,5] administered during surgery and continued through the post-operative recovery period significantly interrupts pericardial adhesion formation in an animal model of post-pericardiotomy fibrosis.

There have been past studies which have implicated the Ang $AT_1$ receptor in the formation of pericardial adhesions and fibrosis. First, through a series of autoradiographic studies, Sun and colleagues have clearly demonstrated that the local production of Ang-II and subsequent activation of the Ang $AT_1$ receptor occurs with the formation of fibrous tissue in the myocardium.[19,20] Second, these investigators have demonstrated previously that in-situ production of Ang-II can occur within the pericardium.[11]

The present inventors have unexpectedly found that institution of Ang $AT_1$ receptor blockade following pericardiotomy significantly reduced pericardial fibrosis and pericardial thickening which invariably occurred in the untreated animals. The present study is the first to demonstrate that Ang $AT_1$ receptor blockade can reduce pericardial fibrosis following a cardiac surgical procedure. Cardiac surgical procedures include but are not limited to pericardiotomy, coronary artery bypass surgery, valve replacement and thoracotomy. The present invention demonstrates that systemic delivery of an Ang $AT_1$ receptor antagonist prior to fibrosis and adherence formation significantly reduces pericardial fibrosis and thickening which occurs following surgical entry into the pericardial space.

While Ang $AT_1$ receptor antagonist administration reduced pericardial fibrosis from untreated values, pericardial thickness remained increased from sham control values. This is likely due to the fact that a number of receptor systems and neurohormonal pathways can contribute to tissue growth and fibrosis.[12] For example, increased sympathetic stimulation and subsequently increased circulating catecholamines as well as the release of aldosterone can significantly influence myocardial fibrosis formation.[12,21] The immediate post-operative period following cardiac surgery is associated with significant neurohormonal activity which likely results in the activation of a number of receptor systems.[13] Thus, Ang $AT_1$ receptor activation is probably only one of several receptor transduction pathways which contributes to pericardial growth and fibrosis following cardiac surgery. Nevertheless, the present inventions shows that Ang $AT_1$ receptor activation is a major contributory factor for pericardial fibrosis and subsequent thickening in the early post-operative period.

During collection of the pericardium, subjective assessment of the degree of pericardial adhesions was performed. In both groups which underwent thoracotomy and pericardiotomy, the relative degree of adhesions and pericardial thickening were reported to be greater than in the sham control group. However, the degree of pericardial adherence to surrounding structures, i.e. myocardium and parietal pleura, appeared to be less in the Ang $AT_1$ receptor blockade group when compared to the untreated group.

Figure 1B:
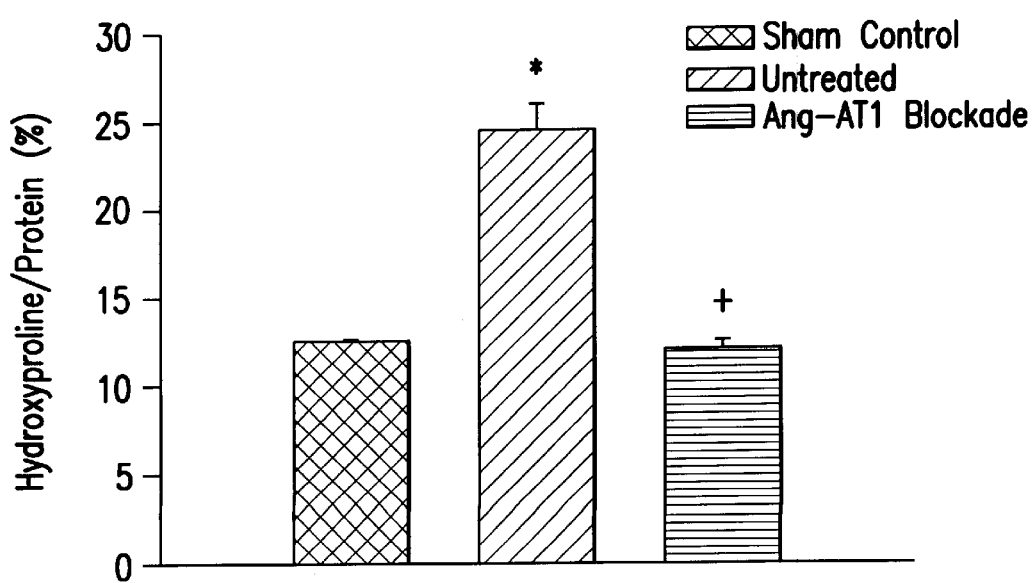
Figure 2A:
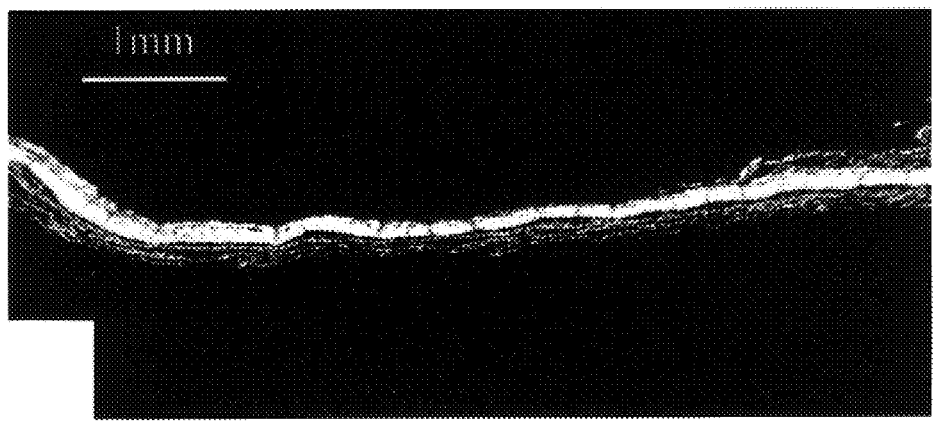
FIG. 2. Representative picrosirius stained pericardial sections taken from a sham control (a), 28 days following pericardiotomy with no treatment (b), and 28 days following pericardiotomy in which Ang $AT_1$ receptor blockade was instituted during the entire post-operative period (c). Pericardial thickening and increased yellow/green staining indicative of collagen deposition, was readily apparent in the untreated post-pericardiotomy sections. In the Ang $AT_1$ receptor blockade group, the degree of pericardial thickening and collagen accumulation appeared reduced from untreated samples. Quantitative histomorphometry was performed on these sections and the results are summarized in FIG. 3.
Figure 2B:
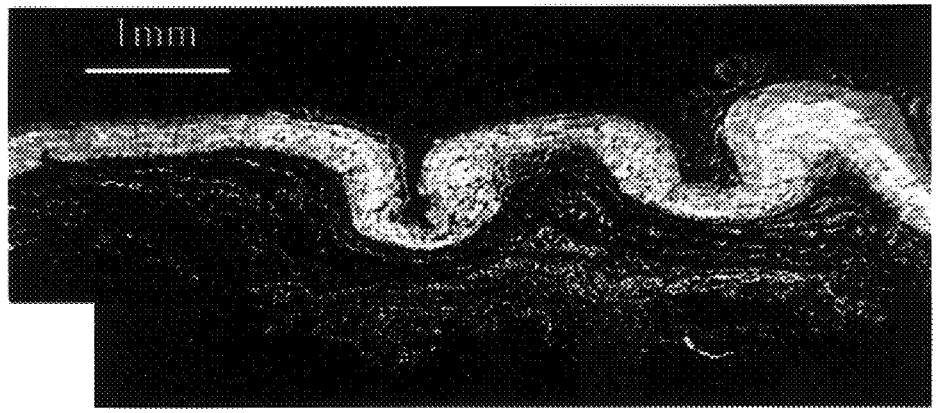
Figure 2C:
Figure 3A:
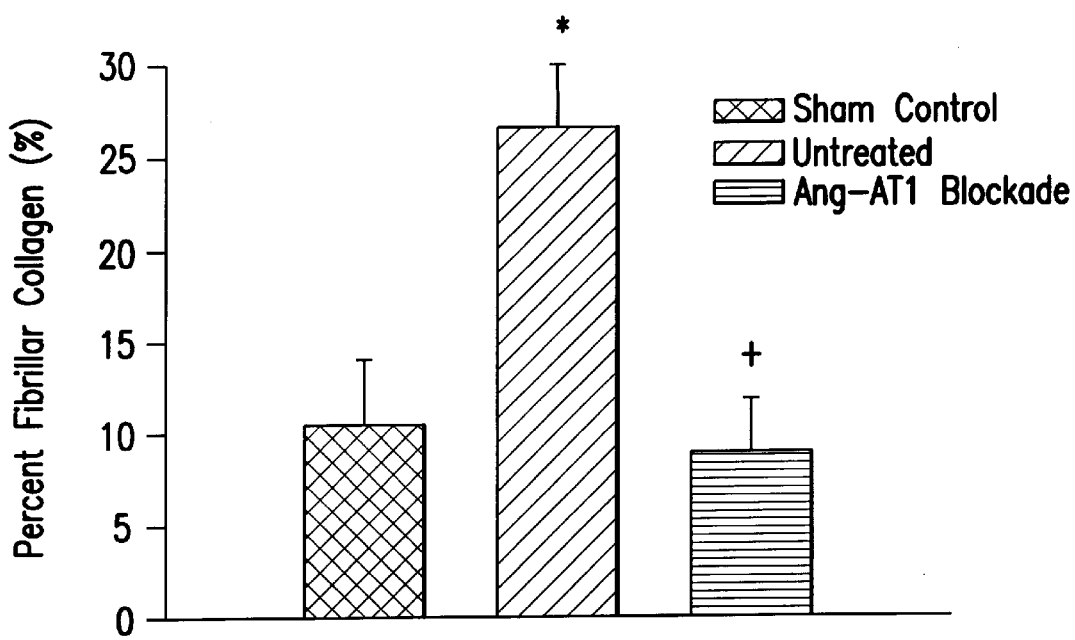
FIG. 3. TOP: The percent area occupied by fibrillar collagen within the pericardium was determined in sham control (n=6), 28 days following pericardiotomy with no treatment (untreated; n=5), and 28 days following pericardiotomy in which Ang $AT_1$ receptor blockade (Ang $AT_1$ blockade; n=5) was instituted during the entire postoperative period. Pericardial fibrillar collagen density was increased by over 2-fold with 28 days following pericardiotomy, and was reduced to within normal values with Ang $A_1$ receptor blockade. BOTTOM: Pericardial thickness was significantly increased over sham control values 28 days following pericardiotomy. Institution of Ang $AT_1$ receptor blockade during the recovery period significantly reduced pericardial thickness. (*$p<0.05$ vs sham control, +$p<0.05$ vs Ang $AT_1$ blockade).
Figure 3B:
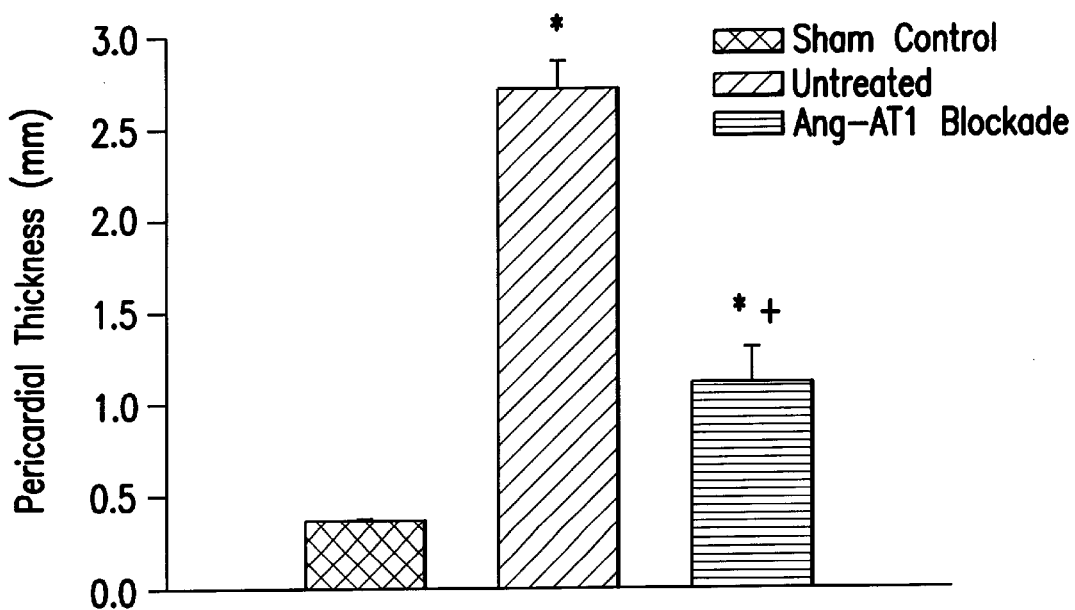

Biochemical analysis of hydroxyproline was performed in the pericardial samples and the results from this analysis is summarized in FIG. 1. When expressed in $\mu$g/mg, a significant increase in hydroxyproline was observed in both groups which underwent pericardiotomy and a 28 day recovery period. However, hydroxyproline content was significantly reduced in the Ang $AT_1$ receptor blockade group when compared to the untreated group. When hydroxyproline was expressed as a percent of total pericardial, a significant increase was observed in the untreated pericardiotomy group when compared to sham controls. However, the relative percent of hydroxyproline was significantly reduced in the Ang $AT_1$ receptor blockade group when compared to untreated values and was similar to control values. Representative photomicrographs of picro-sirius stained pericardial sections from the 3 treatment groups are shown in FIG. 2. Pericardial thickening could be readily observed following 28 days post-pericardiotomy. The degree of pericardial thickening was reduced in the Ang $AT_1$ receptor blockade group. The results from the quantitative histochemical analysis is shown in FIG. 3. The percent of the pericardial section occupied by fibrillar collagen was significantly increased in the untreated pericardiotomy group when compared to sham controls. In the Ang $AT_1$ receptor blockade group, the relative percent of fibrillar collagen was normalized. In the untreated pericardiotomy group, pericardial thickness increased by 2-fold from sham control values. In the Ang $AT_1$ receptor blockade group, pericardial thickness was reduced from untreated pericardiotomy values, but remained increased from sham control values.

In another embodiment of the present invention there is provided a method of reducing fibrosis and adhesion formation following abdominal, pelvic, pleural and lung surgery comprising administering a therapeutically effective amount of an $AT_1$ receptor antagonist or a pharmaceutically acceptable salt thereof either alone or in combination with a pharmaceutically acceptable excipient wherein administration is prior to fibrosis and adherence formation. Abdominal and pelvic surgery includes, but is not limited to, surgery on the viscera, e.g. stomach, small and large intestine, liver, biliary duct, pancreas, kidney, mesentery and peritoneum, twisted ovarian cyst, ectopic gestation, ruptured tubo-ovarian abscess and ureteral stricture which may lead to the formation of fibrous bands and adhesions causing obstruction, strangulation, torsion, infarction and gangrene.

In yet another embodiment of the present invention there is provided a method of reducing fibrosis and adhesion formation which result from pathological conditions which include, but are not limited to, drug-induced retroperitoneal fibrosis e.g. methysergide, post irradiation fibrosis, peritonitis and post-toxic peritonitis adhesiolysis comprising administering prior to the induced pathological condition a therapeutically effective amount of an $AT_1$ receptor antagonist or a pharmaceutically acceptable salt thereof either alone or in combination with a pharmaceutically acceptable excipient.

In still another embodiment of the present invention there is provided a method of reducing fibrosis and adhesion formation which result from all pathologies which stimulate fibroblast proliferation and collagen synthesis, and fibrin formation.

In accordance with another embodiment of the present invention there is provided a method of reducing fibrosis and adhesion formation in a patient following surgery comprising administering a therapeutically effective amount of an $AT_1$ receptor antagonist or a pharmaceutically acceptable salt thereof either alone or in combination with a pharmaceutically acceptable excipient and administering a therapeutically effective amount of an $AT_2$ receptor modulator wherein administration and stimulation are prior to fibrosis and adherence formation.

Angiotensin II plasma levels increase after $AT_1$ receptor blockade in rats and humans.[22,23] Furthermore, Angiotensin II stimulates the $AT_2$ and other unblocked receptors.[24] Stimulation of the $AT_2$ receptor counteracts the effect of the $AT_1$ receptor.[24,25]

AT2 receptor is upregulated in fibrotic areas.[26,27] Stimulation of the $AT_2$ receptor has antifibrotic properties. Therefore, the stimulation of the $AT_2$ receptor will reinforce the effect of the $AT_1$ blockade.[28,29]

$AT_2$ receptor ligands (modulators) include compounds having differing structural features. For example, mention may be made of the compounds which are listed in WO 94/13651, in particular in the compound claims and the final products of the working examples, the subject-matter of which claims is hereby incorporated into the present application by reference to this publication.

The pharmaceutical compositions comprising the active ingredient(s) of the $AT_1$ receptor antagonist are those for enteral, such as oral, which is the preferred route of administration, and also rectal or parenteral administration to warm-blooded animals, the pharmacological active ingredient(s) being present on its own or together with the usual pharmaceutical excipients. The pharmaceutical compositions contain, for example, from about 0.1% to 100%, preferably from about 1% to about 80%, of the active ingredient(s). Pharmaceutical compositions for enteral or parenteral and also for ocular administration are typically those in unit dose forms, such as dragées, tablets, capsules or suppositories and also ampoules. These are prepared in a manner known per se, for example by means of conventional mixing, granulating, sugar-coating, dissolving or lyophilizing methods. Accordingly, pharmaceutical compositions for oral use can be obtained by combining the active ingredient(s) with solid carriers, if desired granulating a mixture obtained, and processing the mixture or granules, if desired or necessary after the addition of suitable excipients, to give tablets or dragée cores.

Suitable carriers are preferably fillers, typically sugars, such as lactose, saccharose, mannitol or sorbitol, cellulose compositions and/or calcium phosphates, e.g. tricalcium phosphate or calciumhydrogen phosphate, furthermore binders, such as starch paste, typically using e.g. corn starch, wheat starch, rice starch or potato starch, gelatin, traga-canth gum, methylcellulose and/or polyvinylpyrrolidone and, if desired, disintegrants, such as the above-mentioned starches, furthermore carboxymethyl starch, crosslinked polyvinylpyrrolidone, agar, alginic acid or a salt thereof, typically sodium alginate. Excipients are primarily flow regulators and lubricants, typically silica gel, talcum, stearic acid or salts thereof, typically magnesium stearate or calcium stearate, and/or polyethylene glycol. Dragée cores are provided with suitable coatings which, if desired, are resistant to gastric juice, using, inter alia, concentrated sugar solutions which optionally contain gum arabic, talcum, polyvinylpyrrolidone, polyethylene glycol and/or titanium dioxide, coating solutions in suitable organic solvents or solvent mixtures or, for the preparation of gastric juice-resistant coatings, solutions of suitable cellulose compositions, typically acetylcellulose phthalate or hydroxypropylmethylcellulose phthalate. Colorants or pigments may be added to the tablets or dragée coatings, for example to identify or indicate different doses of active ingredient(s).

Other pharmaceutical compositions for oral administration are dry-filled gelatin capsules as well as soft closed capsules made of gelatin and a plasticiser, such as glycerol or sorbitol. The dry-filled capsules may contain the active ingredient(s) in the form of granules, typically in admixture with fillers, such as lactose, binders, such as starches, and/or lubricants, such as talcum or magnesium stearate. In soft capsules, the active ingredient(s) is preferably dissolved or suspended in suitable liquids, such as fatty oils, paraffin oil or liquid polyethylene glycols, and stabilisers can also be added.

Suitable pharmaceutical compositions for rectal administration are typically suppositories consisting of a combination of the active ingredient(s) with a suppository base. Suitable suppository bases are, for example, natural or synthetic triglycerides, paraffin hydrocarbons and higher alkanols. Furthermore, gelatin rectal capsules containing a combination of the active ingredient(s) with a base substance may also be used. Suitable base substances are, for example, liquid triglycerides, polyethylene glycols or paraffin hydrocarbons.

Suitable compositions for parenteral administration are primarily aqueous solutions of an active ingredient(s) in water-soluble form, typically a water-soluble salt, and also suspensions of the active ingredient(s), such as appropriate oily injection suspensions, using suitable lipophilic solvents or vehicles, typically fatty oils, e.g. sesame oil, or synthetic fatty acid esters, typically ethyl oleate or triglycerides, or aqueous injection suspensions containing viscosity-increasing substances, e.g. sodium carboxymethylcellulose, sorbitol and/or dextran and, optionally, also stabilisers.

Unit dosage forms for oral administration are preferred, typically tablets or capsules and, in acute treatments, i.v. application forms.

The determination of the dose of the active ingredient(s) necessary to achieve the desired therapeutic effect is within the skill of those who practice in the art. The dose of the active ingredient(s) can depend of various factors, e.g. mode of application, species of warm-blooded animal, age and/or individual state. The estimated normal dose for oral administration to a patient weighing about 75 kg is an approximate dose of about 10 mg to about 250 mg of the $AT_1$ receptor antagonist and about 10 mg to about 250 mg of the $AT_2$ receptor antagonist. The daily dose for oral administration in a unit dose form is preferably about 20 mg to about 160 mg, more preferably about 40 mg or about 80 mg.

EXAMPLES

The following experiments employed a pig model in order to induce post-pericardiotomy fibrosis. This large animal model was chosen since it provided ample pericardial material for study and has been demonstrated to be responsive to modulation of the renin-angiotensin system.[4]

Example 1
Experimental Design and Surgical Procedure

Sixteen Yorkshire pigs (20 kg, male) were used in this study and randomly assigned to the following treatment groups: (1) thoracotomy and pericardiotomy followed by a 28 day recovery period (n=5); (2) thoracotomy and pericardiotomy in which Ang $AT_1$ receptor blockade was instituted throughout the 28 day recovery period (valsartan; Novartis, Basel, 60 mg/day, n=5) (3) sham controls (n=6). For the surgical procedures, the animals were anesthetized with isoflurane (3%/1–5 L/min) and a mixture of nitrous oxide and oxygen (50:50), intubated with a cuffed endotracheal tube and ventilated at a flow rate of 22 ml/Kg/minute and a respiratory rate of 15/minute. Through a left thoracotomy, the left anterior aspect of the pericardium was incised in a longitudal pattern from the origin of the great vessels to the apex of the left ventricle. The pericardial and thoracic cavity were irrigated with 500 cc of warm saline containing 1 g of cefazolin (SmithKline Beecham, Pa.) and the pericardium was approximated with a single silk suture. The thoracic incision was closed in layers, the chest evacuated of air and 1 g of cefazolin was administered systemically. In the Ang $AT_1$ receptor blockade treatment group, osmotic minipumps (2ML1, Alza Corp., Palo Alto, Calif.) were implanted in the peritoneum in order to maintain a constant plasma valsartan level.[14] All of the animals were cared for in identical fashion during the 28 day post-operative period. Following collection of the pericardial samples as described in the following paragraph, the animals were euthanized with an overdose of isoflurane (5%) and nembutal (500 mg). All animals were cared for in accordance with the National Institutes of Health "Guide for the Care and Use of Laboratory Animals" (National Research Council, Washington, 1996).
Pericardial Collection and Analysis On day 28 following the initial surgical procedure, the animals were deeply anesthetized with 5% isoflurane and intubated. Through a stemotomy, the anterior aspect of the thoracic cavity was carefully exposed in order to prevent any mechanical disruption of the pericardium. The relative degree of pericardial adhesions and adherence to the myocardium and surrounding structures was qualitatively assessed. The pericardium was then completely excised in 2 equal sections and quickly rinsed in chilled saline. One pericardial section was immediately frozen in liquid nitrogen and stored at −70° C. until analysis and the other section was immersed in 3.7% buffered formalin for histochemical studies. The pericardial sections which were subjected to biochemical or histochemical analysis were alternated with each case.

Biochemical analysis of the collected pericardial samples was performed by determining hydroxyproline content[16] and amino acid found primarily in fibrillar collagen. Briefly, the pericardial samples were weighed and lyophilized. The sections were then hydrolyzed and measured spectrophotometrically (550 nm) following reaction with Ehrlich's reagent.[16] The total protein content of the hydrolyzed tissue was also determined by a standardized colorimetric assay (Bio-Rad Protein Assay, Bio-Rad, Richmond, Calif.). The resultant hydroxyproline values were expressed as $\mu$g/mg of pericardium as well as a percent of hydroxyproline to total pericardial protein content.

Light microscopic examination was performed on the fixed pericardial samples in order to determine pericardial thickness and the percent area occupied by fibrillar collagen. The samples were mounted in 2×3 cm wax blocks in order that the full thickness of the pericardial section was properly exposed. Full sections were cut from the embedded samples and stained using the picro-sirius histochemical technique.[7,18] The stained sections were imaged and digitized at a low magnification (10×) in order to measure pericardial thickness. The images were digitized using a Kodak DCS 420 digital camera (Kodak Inc., Rochester, N.Y.) which provided a high resolution image (1500×1000 pixels). Pericardial thickness was determined from a minimum of 10 linear measurements taken across the pericardium (Gel-Pro Analyzer, Media Cybernetics, Silver Spring, Md.). For the determination of fibrillar collagen, the sections were imaged at 320× using a polarization filter (Ziess, Germany) using methods described previously.[17,18] The percent area of fibrillar collagen was computed from 15 random fields from each section using the image analysis system described previously.

Data Analysis

All of data was collected and coded until the completion of the study. At which time, the code was broken and summary statistics performed. Biochemical and histochemical measurements of the pericardium were first compared between the 3 groups using analysis of variance (ANOVA). If the ANOVA revealed significant differences, pairwise tests of individual group means were compared using Student-Neuman-Keuls test. All statistical procedures were performed using the BMDP statistical software package (BMDP Statistical Software Inc., Los Angeles, Calif.). Results are presented as mean±standard error of the mean (SEM). Values of $p<0.05$ were considered to be statistically significant.

Example 2

Formulations

Formulation Example 1:

Film-Coated Tablets:

| Components | Composition Per Unit (mg) | Standards |
|---|---|---|
| Granulation | | |
| Valsartan [= active ingredient] | 80.00 | |
| Microcrystalline cellulose/ Avicel pH 102 | 54.00 | NF, Ph. Eur |
| Crospovidone | 20.00 | NF, Ph. Eur |
| Colloidal anhydrous silica/ Colloidal silicon dioxide/Aerosil 200 | 0.75 | Ph. Eur/ NF |
| Magnesium stearate | 2.5 | NF, Ph. Eur |
| Blending | | |
| Colloidal anhydrous silica/ Colloidal silicon dioxide/Aerosil 200 | 0.75 | Ph. Eur/ NF |
| Magnesium stearate | 2.00 | NF, Ph. Eur |
| Coating | | |
| Purified water*⁾ | — | |
| DIOLACK pale red 00F34899 | 7.00 | |
| Total tablet mass | 167.00 | |

*⁾Removed during processing.

The film-coated tablet is manufactured e.g. as follows:

A mixture of Valsartan, microcrystalline cellulose, crospovidone, part of the colloidal anhydrous silica/colloidal silicon dioxide/Aerosile 200, silicon dioxide and magnesium stearate is premixed in a diffusion mixer and then sieve through a screening mill. The resulting mixture is again pre-mixed in a diffusion mixer, compacted in a roller compactor and then sieve through a screening mill. To the resulting mixture, the rest of the colloidal anhydrous silica/ colloidal silicon dioxide/Aerosil 200 are added and the final blend is made in a diffusion mixer. The whole mixture is compressed in a rotary tabletting machine and the tablets are coated with a film by using Diolack pale red in a perforated pan.

Formulation Example 2:

Film-coated tablets:

| Components | Composition Per Unit (mg) | Standards |
|---|---|---|
| Granulation | | |
| Valsartan [= active ingredient] | 160.00 | |
| Microcrystalline cellulose/ Avicel PH 102 | 108.00 | NF, Ph. Eur |
| Crospovidone | 40.00 | NF, Ph. Eur |
| Colloidal anhydrous silica/ Colloidal silicon dioxide/Aerosil 200 | 1.50 | Ph. Eur/ NF |
| Magnesium stearate | 5.00 | NF, Ph. Eur |
| Blending | | |
| Colloidal anhydrous silica/ Colloidal silicon dioxide/Aerosil 200 | 1.50 | Ph. Eur/ NF |
| Magnesium stearate | 4.00 | NF, Ph. Eur |
| Coating | | |
| Opadry Light Brown 00F33172 | 10.00 | |
| Total tablet mass | 330.00 | |

The film-coated tablet is manufactured e.g. as described in Formulation Example 1.

Formulation Example 3:

Film-Coated Tablets:

| Components | Composition Per Unit (mg) | Standards |
|---|---|---|
| Core: Internal phase | | |
| Valsartan [= active ingredient] | 40.00 | |
| Silica, colloidal anhydrous (Colloidal silicon dioxide) [= Glidant] | 1.00 | Ph. Eur, USP/NF |
| Magnesium stearate [= Lubricant] | 2.00 | USP/NF |
| Crospovidone [Disintegrant] | 20.00 | Ph. Eur |
| Microcrystalline cellulose [= Binding agent] | 124.00 | USP/NF |
| External phase | | |
| Silica, colloidal anhydrous, (Colloidal silicon dioxide) [= Glidant] | 1.00 | Ph. Eur, USP/NF |
| Magnesium stearate [Lubricant] | 2.00 | USP/NF |
| Film coating | | |
| Opadry® brown OOF 16711*⁾ | 9.40 | |
| Purified Water**⁾ | — | |
| Total tablet mass | 199.44 | |

*⁾The composition of the Opadry® brown OOF16711 coloring agent is tabulated below.
**⁾Removed during processing Opadry® Composition:

| Ingredient | Approximate % Composition |
|---|---|
| Iron oxide, black (C.I. No. 77499, E 172) | 0.50 |
| Iron oxide, brown (C.I. No. 77499, E 172) | 0.50 |
| Iron oxide, red (C.I. No. 77491, E 172) | 0.50 |
| Iron oxide, yellow (C.I. No. 77492, E 172) | 0.50 |
| Macrogolum (Ph. Eur) | 4.00 |
| Titanium dioxide (C.I. No. 77891, E 171) | 14.00 |
| Hypromellose (Ph. Eur) | 80.00 |

The film-coated tablet is manufactured e.g. as described in Formulation Example 1.

Formulation Example 4:
Capsules:

| Components | Composition Per Unit (mg) |
|---|---|
| Valsartan [= active ingredient] | 80.00 |
| Microcrystalline cellulose | 25.10 |
| Crospovidone | 13.00 |
| Povidone | 12.50 |
| Magnesium stearate | 1.30 |
| Sodium lauryl sulphate | 0.60 |
| Shell | |
| Iron oxide, red (C.I. No. 77491, EC No. E 172) | 0.123 |
| Iron oxide, yellow (C.I. No. 77492, EC No. E 172) | 0.123 |
| Iron oxide, black (C.I. No. 77499, EC No. E 172) | 0.245 |
| Titanium dioxide | 1.540 |
| Gelatin | 74.969 |
| Total tablet mass | 209.50 |

The tablet is manufactured e.g. as follows:

Granulation/Drying

Valsartan and microcrystallin cellulose are spray-granulated in a fluidized bed granulator with a granulating solution consisting of povidone and sodium lauryl sulphate dissolved in purified water. The granulate obtained is dried in a fluidized bed dryer.

Milling/Blending

The dried granulate is milled together with crospovidone and magnesium stearate. The mass is then blended in a conical screw type mixer for approximately 1 0 minutes.

Encapsulation

The empty hard gelatin capsules are filled with the blended bulk granules under controlled temperature and humidity conditions. The filed capsules are dedusted, visually inspected, weight checked and guaranteed until by Quality assurance department.

Formulation Example 5:
Capsules:

| Components | Composition Per Unit (mg) |
|---|---|
| Valsartan [= active ingredient] | 160.00 |
| Microcrystalline cellulose | 50.20 |
| Crospovidone | 26.00 |
| Povidone | 25.00 |
| Magnesium stearate | 2.60 |
| Sodium lauryl sulphate | 1.20 |
| Shell | |
| Iron oxide, red (C.I. No. 77491, EC No. E 172) | 0.123 |
| Iron oxide, yellow (C.I. No. 77492, EC No. E 172) | 0.123 |
| Iron oxide, black (C.I. No. 77499, EC No. E 172) | 0.245 |
| Titanium dioxide | 1.540 |
| Gelatin | 74.969 |
| Total tablet mass | 342.00 |

The formulation is manufactured e.g. as described in Formulation Example 4.

Formulation Example 6:

Hard Gelatin Capsule:

| Components | Composition Per Unit (mg) |
|---|---|
| Valsartan [= active ingredient] | 80.00 |
| Sodium laurylsulphate | 0.60 |
| Magnesium stearate | 1.30 |
| Povidone | 12.50 |
| Crospovidone | 13.00 |
| Microcrystalline cellulose | 21.10 |
| Total tablet mass | 130.00 |

Although the present invention has been described in considerable detail with reference to certain preferred versions thereof, other versions are possible without departing from the spirit and scope of the preferred versions contained herein.

All references referred to herein and set forth in the attached reference page, are hereby incorporated by reference in their entirety.

REFERENCES

1. Allen K B, Matheny R G, Robinson R J, Heimansohn D A, Shaar C J. Minimally invasive versus conventional reoperative coronary artery bypass. Ann Thorac. Surg 64:616–622, 1997.
2. Tuula S O, Kurki T S, Kataja M. Preoperative prediction of postoperative morbidity in coronary artery bypass grafting. Ann Thorac Surg 61;1740–1745, 1996.
3. Christenson J T, Schmuziger M, Simonet F. Reoperative coronary artery bypass procedures: risk factors for early mortality and late survival. Eur J Cardiothoracic Surg 11:129–133, 1997.
4. Nkere U U, Whawell S A, Sarraf C E, Schofield J B, Thompson J N. Taylor, K M. Pericardial trauma and adhesions in relation to reoperative cardiac surgery. Thorac Cardiovasc Surgeon 43:338–346, 1995.
5. Novez L, Skotnick S H, Lacquet L K. Morbidity and mortality in 200 consecutive coronary reoperations. Eur J Cardiothoracic Surg 11:528–532, 1997.
6. The Society of Thoracic Surgeons. Data Analysis Of The Society Of Thoracic Surgeons National Cardiac Surgery Database: The Seventh Year. Summit Medical. Minnetonka, Minn. January 1998.
7. A Seeger J M, Kaelin L D, Staples E M. Yaacobi Y, Bailey J C. Normann S, Burns J W, Goldberg E P. Prevention of postoperative pericardial adhesions using tissue-protective solutions. J Surg Res 68:63–66, 1997.
8. Hurle A, de la Vega M, Feijoo JJ, Ray V G, Abad C. Ponce G, Perez-Arellano J L. Effect of physical protection on the mesothelial integrity of the pericardium. Ann Thorac Surg 63:1091–1094, 1997.
9. Duvernoy O, Maim T, Ramstrom J, Bowald S. A biodegradable patch used as a pericardial substitute after cardiac surgery: 6- and 24-month evaluation with CT. Thorac Cardiovasc Surgeon 43:271–274,1995.
10. Weber K T, Sun Y, Katwa I-C. Myofibroblasts and local angiotensin II in rat cardiac tissue repair. Int J Biochem Cell Biol 29:31–42, 1997.
11. Ou R, Sun Y, Ganjam V K, Weber K T. In situ production of angiotensin II by fibrosed rat pericardium. J Mol Cell Cardiol 28:1319–1327, 1996.
12. Weber K T, Anversa P, Armstrong P W, Brilla C G, Burnett JC, Cruickshank J M, Devereux, R B, Giles T D.

Korsgaard N, Leier C V, Mendelsohn F A O, Motz, W H, Mulvany M J, and Strauer B E. Remodeling and reparation of the cardiovascular system. J Am Coll Cardiol. 20:3–16, 1992.
13. Reves J G, Karp R B, Buttner E E, Tosone S, Smith L R, Samuelson P N, et al. Neuronal and adrenomedullary catecholarnine release in response to cardiopulmonary bypass in man. Circulation 66:49–55,1982.
14. Spinale F G, de Gasparo M, Whitebread S, Hebbar L, Clair M J, Melton M, Krombach R S, Mukhedee R, lannini J P, 0 S J. Modulation of the renin-angiotensin pathway through enzyme inhibition and specific receptor blockade in pacing Induced heart failure. I. Effects on left ventricular performance and neurohormonal systems. Circulation 96:2385–2396,1997.
15. Criscione L, de Gasparo M, Bohimayer P, Whitebread S, Ramjoue H R, Wood J. Pharmacological profile of valsartan: a potent, orally active, nonpeptide
16. Spinale F G, Tomita M, Zellner J L, Cook J C, Crawford F A, Zile M R. Collagen remodeling and changes in LV function during development and recovery from supraventricular tachycardia. Am J Physiol 261:H308–H318, 1991.
17. Whittaker P, Kloner R A, Boughner D F R, Pickering J G. Quantitative assessment of myocardial collagen with picrosirius red staining and circularly polarized light. Bas Res Cardiol 89:397–410, 1994.
18. Spinale F G, Coker M L, Thomas C V, Walker J D, Mukherjee R, Hebbar L. Time dependent changes in matrix metalloproteinase activity and expression during the progression of congestive heart failure: relation to ventricular and myocyte function. Circulation Research, 82:482–495, 1998.
19. Sun Y, Weber K T. Cells expressing angiotensin II receptors in fibrous tissue of rat heart. Cardiovasc Res 31:518–525, 1996.
20. Sun Y. Ramires R J, Zhou G, Ganjam V K, Weber K T. Fibrous tissue and angiotensin II. J Mol Cell Cardiol 29:2001–2012, 1997.
21. Weber K T. Brilla C G. Pathological hypertrophy and cardiac interstitium, Fibrosis and renin-angiotensin system. Circulation 83:1849–1865, 1991.
22. Bunkenburg B, et al. Hypertension 1991, 18, 278–288.
23. Goldberg M R, et al. Hypertension 1995, 25, 37–47.
24. deGasparo M, and Levens N. Pharmacol Tox 1998, 82, 257–271.
25. Chung O et al. Kidney Int 1998, 54, Suppl 67, S95-S99.
26. Brink M et al. J Mol Cell Cardiol 1996, 28, 1789–1799.
27. Tsutsumi Y et al. Circ Res 1998, 83, 1035–1046.
28. Ohkubo N et al. Circulation 1997, 96, 3954–3962.
29. Ma J et al. Kidney Int 1998, 43, 937–944.

What is claimed is:

1. A method for reducing fibrosis and adhesion formations in a surgical patient comprising administering a therapeutically effective amount of valsartan prior to fibrosis and adhesion formation.

2. The method of claim 1 wherein valsartan is combined with a pharmaceutically acceptable excipient.

3. The method of claim 1 wherein the surgery is performed on an organ selected from the group consisting of stomach, small intestine, large intestine, liver, biliary duct, pancreas, kidney, mesentery, peritoneum, ovaries and ureters.

4. The method of claim 1 wherein administration begins during surgery and continues through the post-operative recovery period.

5. A method for reducing pericardial fibrosis and adhesion formations in a cardiac surgery patient comprising administering a therapeutically effective amount of valsartan prior to fibrosis and adhesion formation.

6. The method of claim 5 wherein the cardiac surgery is selected from the group consisting of limited to pericardiotomy, coronary artery bypass surgery, valve replacement and thoracotomy.

7. The method of claim 5 wherein valsartan is combined with a pharmaceutically acceptable excipient.

8. The method of claim 5 wherein administration begins during surgery and continues through the post-operative recovery period.

9. A method for reducing fibrosis and adhesion formations in a patient with an induced pathological condition selected from the group consisting of drug-induced retroperitoneal fibrosis, post irradiation fibrosis, peritonitis and post-toxic peritonitis adhesiolysis comprising administering a therapeutically effective amount of valsartan prior to fibrosis and adhesion formation.

10. The method of claim 9 wherein valsartan is combined with a pharmaceutically acceptable excipient.

* * * * *